(12) United States Patent
Chavan et al.

(10) Patent No.: US 9,562,030 B2
(45) Date of Patent: Feb. 7, 2017

(54) PROCESS FOR THE SYNTHESIS OF OLOPATADINE

(71) Applicant: Council of Scientific and Industrial Research, New Delhi (IN)

(72) Inventors: Subhash Prataprao Chavan, Pune (IN); Pradeep Bhaskarrao Lasonkar, Pune (IN)

(73) Assignee: Council of Scientific and Industrial Research, New Delhi (IN)

(*) Notice: Subject to any disclaimer, the term of this patent is extended or adjusted under 35 U.S.C. 154(b) by 0 days.

(21) Appl. No.: 14/778,311

(22) PCT Filed: Mar. 19, 2014

(86) PCT No.: PCT/IN2014/000173
§ 371 (c)(1),
(2) Date: Sep. 18, 2015

(87) PCT Pub. No.: WO2014/147647
PCT Pub. Date: Sep. 25, 2014

(65) Prior Publication Data
US 2016/0280677 A1    Sep. 29, 2016

(30) Foreign Application Priority Data
Mar. 19, 2013 (IN) .............................. 803/DEL/2013

(51) Int. Cl.
*C07D 313/12* (2006.01)

(52) U.S. Cl.
CPC .................... *C07D 313/12* (2013.01)

(58) Field of Classification Search
CPC .................................................. C07D 313/12
USPC .......................................................... 549/354
See application file for complete search history.

(56) References Cited

U.S. PATENT DOCUMENTS

| 2007/0105234 A1 | 5/2007 | Swiderski et al. |
| 2012/0004426 A1 | 1/2012 | Silva Guisasola et al. |
| 2012/0016138 A1 | 1/2012 | Guidi et al. |

FOREIGN PATENT DOCUMENTS

| EP | 2145882 | 1/2010 |
| WO | WO-2006/010459 | 2/2006 |
| WO | WO-2007/105234 A2 | 9/2007 |
| WO | WO-2007/142810 | 12/2007 |
| WO | WO-2010/121877 | 10/2010 |
| WO | WO-2011/033532 | 3/2011 |
| WO | WO-2014/147647 | 9/2014 |

OTHER PUBLICATIONS

Bosch, Joan, et al., "Stereoselective Syntheses of the Antihistaminic Drug Olopatadine and Its E-Isomer", *J. Org. Chem.*, 77, (2012), 6340-6344.

Chavan, Subhash, et al., "A Simple Synthesis of the Novel Antihistaminic Drug Olopatadine Hydrochloride", *Synthesis*, 45(24), (2013), 3399-3403.

(Continued)

*Primary Examiner* — T. Victor Oh
(74) *Attorney, Agent, or Firm* — Schwegman Lundberg & Woessner, P.A.

(57) ABSTRACT

The present invention provides a process for the synthesis of olopatadine. Further, the invention discloses a process that results in improved yield of the desired Z isomer.

3 Claims, 1 Drawing Sheet

(56) References Cited

OTHER PUBLICATIONS

Nishimura, Koichiro, et al., "A New Efficient Synthetic Route for the Synthesis of the Antiallergic Drug, Olopatadine Hydrochloride, via Stereospecific Palladium-Catalyzed Reaction", *Org. Process Res. Dev.*, 16(2), (2012), 225-231.
Ohshima, Etsuo, et al., "Synthesis of a Dibenz[b,e]oxepin-Bovine Serum Albumin Conjugate for Radioimmunoassay of KW-4679 ((Z)-11-[3-(Dimethylamino)propylidene]-6,11-dihydrodibenz[b,e]oxepin-2-acetic Acid Hydrochloride).", *Chem. Pharm. Bull.*, 40(9), (1992), 2552-2554.
Oshima, Etsuo, et al., "Synthesis and Antiallergic Activity of 11-(Aminoalkylidene)-6,11-dihydrodibenz[b,e]oxepin Derivatives", *Journal of Medicinal Chemistry*, 35(11), (1992), 2074-2084.
Reddy, Chada R., et al., "A Facile One-Pot Access to Dibenzo[b,e]oxepines by a Lewis Acid Catalysed Tandem Reaction", *Eur. J. Org. Chem.*, (2011), 2133-2141.
"International Application No. PCT/IN2014/000173, International Search Report mailed Jul. 11, 2014", (Jul. 11, 2014), 4 pgs.

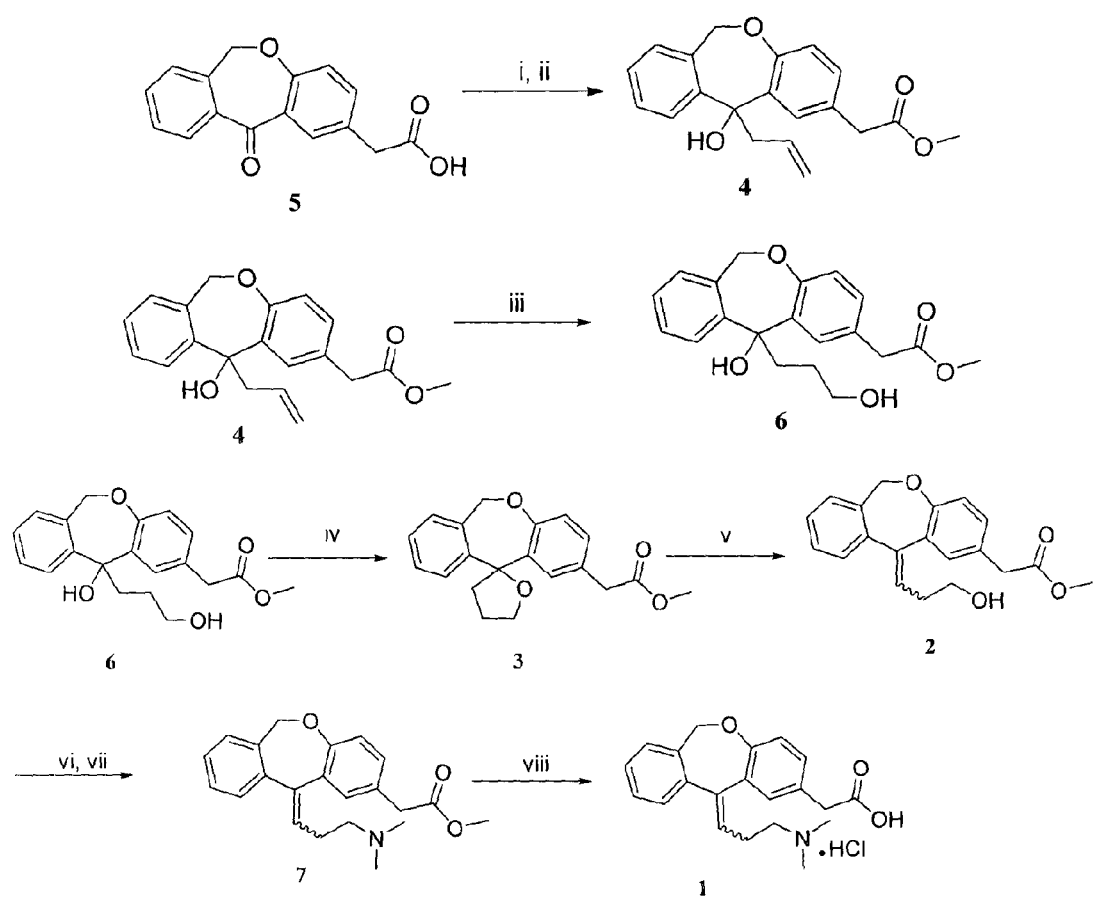

PROCESS FOR THE SYNTHESIS OF OLOPATADINE

PRIORITY CLAIM TO RELATED APPLICATIONS

This application is a U.S. national stage application filed under 35 U.S.C. §371 from International Application Serial No. PCT/IN2014/000173, which was filed 19 Mar. 2014, and published as WO2014/147647 on 25 Sep. 2014, and which claims priority to India Application No. 0803/DEL/2013, filed 19 Mar. 2013, which applications and publication are incorporated by reference as if reproduced herein and made a part hereof in their entirety, and the benefit of priority of each of which is claimed herein.

FIELD OF THE INVENTION

This invention relates to a process for the synthesis of olopatadine. Particularly the invention relates to a process that results in improved yield of the desired Z isomer.

BACKGROUND AND PRIOR ART OF THE INVENTION

Olopatadine is an antihistaminic drug, used for the treatment of ocular symptoms of seasonal allergic conjunctivitis. Olopatadine was developed by Kyowa Hakko Kirin Co. Ltd. and produced commercially by the synthetic route using Wittig reaction as key step. Although both olopatadine Z and E isomers show similar $H_1R$ affinities, only the Z isomer is the marketed drug. Because of antiallergic activity many chemists are involved developing a better process for Z-isomer of olopatadine (FIG. 1).

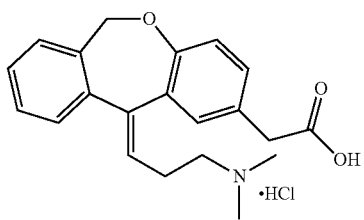

Structure of Olopatadine Hydrochloride

Several literature reports are available for process of synthesis of olopatadine. In most of the processes, the side chains was introduced by 'Grignard reaction' or by 'Wittig reaction', refer WO 2011/033532, US 2007/105234 and WO 2010/0121877, US 20120016138 respectively. In previous approaches the main drawback was the Z/E stereoselectivity. These references describe the usage of Grignard and/or Wittig reactions which necessitates the usage of dry solvents and the reactions to be performed at low temperatures and make use of hazardous reagents like n-butyl lithium, hexyl lithium, sodium hydride etc. and Grignard reagents which are difficult to perform on an industrial scale with lot of risk elements incorporated in them and hence are not desirous. In addition excess of reagents are required and the process is very long making it expensive.

References may be made to journal entitled "A New Efficient Synthetic Route for the Synthesis of the Antiallergic Drug, Olopatadine Hydrochloride, via Stereospecific Palladium-Catalyzed Reaction" in Org. Process Res. Dev. 2012, 16, 225-231 reports a new practical and efficient synthetic route for the synthesis of olopatadine hydrochloride via the intramolecular stereospecific seven-membered ring cyclization from an alkyne intermediate using palladium catalyst and hydride source. Furthermore, the optimization of that key stereospecific reaction was examined by design of experiment (DoE), and the desired Z-isomer could be obtained with high yield. While the reference make use of expensive Pd metal to access olopatadine, use of expensive reactant like iodine and silver sulphate for iodination making it less attractive from commercial standpoint.

References may be made to patent application US 2012/0004426 A1, wherein process for obtaining esters and amides of Olopatadine useful for the production of Olopatadine and salts thereof. This method also utilises Wittig reaction and use of hazardous metal hydrides like NaH in the range of 1-1.6 equiv. and dry solvents and preferably a combination of THF and dipolar aprotic solvent like DMA, DMF which becomes difficult to handle on an industrial scale. Moreover the isopropyl esters as well as amides utilised are not easy to prepare and finally require harsh conditions for deprotection to liberate acid.

Recently, Bosch et. al. in J. Org. Chem., 2012, 77, 6340-6344 utilized stereoselective Heck reaction to control stereochemistry of Z-isomer by the intramolecular cyclization of the E-alkene intermediate.

Nishimura et. al. in Org. Process Res. Dev. 2012, 16, 225-231 and WO 2006/010459 also reported a stereospecific route using palladium catalyst. In the Nishimura synthetic route, the Z-stereoselectivity was controlled by intramolecular stereospecific seven-membered ring cyclization from an alkyne intermediate using palladium catalyst.

Article titled, "A Facile One-Pot Access to Dibenzo[b,e] oxepines by a Lewis Acid Catalysed Tandem Reaction" by Chada R. Reddy, Palacherla Ramesh, Nagavaram N. Rao, Saiyed A. Ali in European Journal of Organic Chemistry Volume 2011, Issue 11, pages 2133-2141, April 2011 reports Dibenzo[b,e]oxepine derivatives constructed efficiently by one-pot tandem carbon-carbon bond formation reactions. First, 2-(3,5-dimethoxybenzyloxy)benzaldehydes were treated with various nucleophiles under $I_2$ catalysis and then 1-(3,5-dimethoxybenzyloxy)-3,5-dimethoxybenzene was treated with several aromatic as well as heteroaromatic aldehydes under $BF_3.Et_2O$ catalytic conditions to provide dibenzo[b,e]oxepines in good yields. This publication although describes a general route to access Dibenzo[b,e] oxepines it works only if two electron donating groups are present on one aromatic ring. The reaction does not work for unsubstituted aromatic ring and hence can not be applied for olopatadine synthesis. The authors in this publication have not described any route for the synthesis of olopatadine.

Thus a review of reported method of synthesis of olopatadine suffer from several drawbacks including using expensive catalysts such as Palladium or use of hazardous reagents such as Grignard reagents or as in Wittig reaction or result in poor yields of the preferred Z isomer. Some routes are operationally difficult to perform on a large scale. The present invention addresses the drawbacks as listed herein.

OBJECTIVE OF THE INVENTION

Main object of the present invention is to provide a process for synthesis of olopatadine wherein the process results in improved yields of the preferred Z isomer.

Another object of the invention is to provide a process for synthesis of olopatadine avoiding hazardous reactions and reagents.

BRIEF DESCRIPTION OF THE DRAWING

FIG. 1 is a scheme of the process steps for synthesis of olopatadine, wherein:

i) SOCl$_2$, MeOH, 24 hours, RT, 98%;
ii) Zn, Allyl bromide, DMF, 2 hours, 91%.
iii) 9-BBN, NaOH, H$_2$O$_2$, THF, 24 h, 84%.
iv) p-TSA, DCM, 10 minutes, RT, 99%;
v) AlCl$_3$, DCM, 0° C.-RT, 7 hours, 95%;
vi) MsCl, Pyridine, 2 hours;
vii) 50% Me$_2$NH, MeOH, reflux, 3 hours, 84% over two steps;
viii) Ref. Ohshima, E; Otaki, S; Sato, H; Kumazawa, T; Obase, H; Ishii, A; Ishii, H; Ohmori, K; and Hirayama, N J. *J. Med Chem.* 1992, 35, 2074.

SUMMARY OF THE INVENTION

Accordingly, present invention relates to an improved process for synthesis of olopatadine comprising the steps of:

a. treating Isoxepac (5), 2-(11-oxo-6,11-dihydrodibenzo[b,e]oxepin-2-yl)acetic acid with thionyl chloride in the ratio ranging between 2 to 4 in the presence of alcohol at room temperature in the range of 15 to 30° C. for period in the range of 12 to 24 hours to yield corresponding ester;

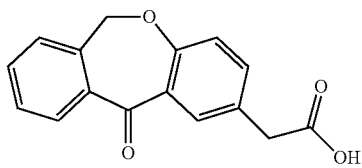

5 b. treating ester of step (a) with allyl bromide using Zn in a solvent conducting Barbier reaction to obtain allylic alcohol 4;

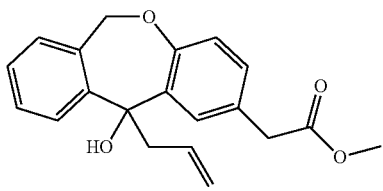

4 c. Hydroborating the allyl alcohol (4) as obtained in step (b) using 9-BBN (9-Borabicyclo(3.3.1)nonane)/diborane quenched by sodium hydroxide and hydrogen peroxide to obtain diol 6;

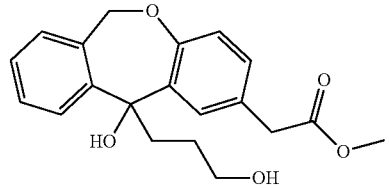

6 d. treating diol 6 as obtained in step (c) with catalytic p-TSA instantly form a spiro tetrahydrofuran ring 3 in almost quantitative yield;

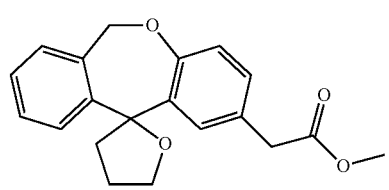

3 e. treating compound 3 as obtained in step (d) with AlCl$_3$ as Lewis acid in DCM to yield olefin 2 and satisfactory E/Z ratio of 1 to 1.5;

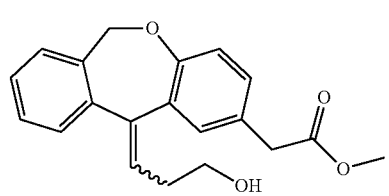

2 f. subjecting compound 2 of step (e) to mesylation and dimethyl amination resulted in compound 7 in the range of 55 to 60%;

g. converting compound 7 as obtained in step (f) to compound 1 by known techniques with E:Z ratio of 1:1.5.

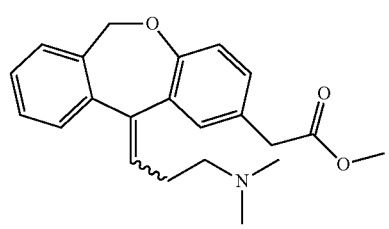

7

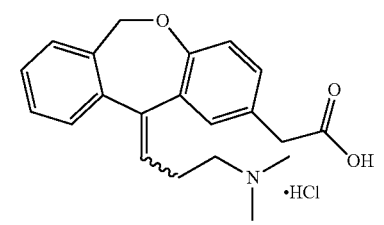

1

In another embodiment of the present invention, alcohol used in step (a) is methanol.

In yet another embodiment of the present invention, solvent used in step (b) is dimethyl formamide (DMF).

DETAILED DESCRIPTION OF THE INVENTION

Present invention provides a process for synthesis of olopatadine resulting in yields of greater than 50%, with the E:Z of 1:1.5.

In accordance to FIG. 1, the process for the synthesis of olopatadine comprises:

a. treating Isoxepac (5), 2-(11-oxo-6,11-dihydrodibenzo[b,e]oxepin-2-yl)acetic acid with thionyl chloride in the presence of methanol at room temperature in the range of 15 to 30° C. for 24 hours to yield corresponding ester;

b. conducting Barbier reaction on the ester of step (a) with allyl bromide using Zn in a solvent, to form allylic alcohol 4;

c. conducting Hydroboration of 4 using 9-BBN/diborane which was quenched by sodium hydroxide and hydrogen peroxide, affording diol 6.

d. treating the diol 6 with catalytic p-TSA instantly form a spiro tetrahydrofuran ring 3 in almost quantitative yield.

e. treating compound 3 with $AlCl_3$ as Lewis acid in DCM to yield olefin 2 in excellent yield and satisfactory E/Z ratio (1/1.5);

f. subjecting compound 2 of step (e) to mesylation and dimethyl amination resulted in compound 7, which was converted to compound 1 by known techniques.

EXAMPLES

Following examples are given by way of illustration and therefore should not be construed to limit the scope of the invention.

Example 1

2-(11-oxo-6,11-dihydrodibenzo[b,e]oxepin-2-yl)acetic acid (5 g, 18.65 mmol) was dissolved in methanol (100 mL) and cooled at 0° C. Thionyl chloride (2.06 mL, 27.98 mmol) was added dropwise during a half hour period and the solution was stirred at room temperature (25° C.) for 24 h. The solvent was evaporated almost to dryness and the residue was partitioned between dichloromethane (50 mL) and saturated sodium bicarbonate solution (50 mL). The organic layer was dried over anhydrous $Na_2SO_4$, filtered and concentrated under reduced pressure, giving ketoester, which was used without further purification.

Example 2

To a stirred mixture of Isoxepac ester (5 g, 17.66 mmol) and zinc (3.44 g, 53 mmol) in DMF (50 mL), allyl bromide (1.66 mL, 19.43 mmol) was added at 0° C. After 2 hours the reaction mixture was filtered to remove the remaining zinc, 10% hydrochloric acid (20 mL) was added and organic layer was separated. The aqueous layer extracted with small portions of EtOAc, the combined organic extracts were dried over $Na_2SO_4$ and concentrated in vacuo. The resulting liquid was purified by column chromatography (pet ether-ethyl acetate, 8:2) to give compound 4 (5.2 g, 91%) as thick colorless oil.

Colorless liquid; $^1$H NMR (200 MHz, $CDCl_3$+$CCl_4$): δ 2.86-2.97 (m, 1H), 3.34-3.44 (m, 1H), 3.60 (s, 2H), 3.68 (s, 3H), 5.04 (d, J=15.5 Hz, 1H), 5.09-5.18 (m, 2H), 5.47 (d, J=15.5 Hz, 1H), 5.35-5.56 (m, 1H), 6.90-7.00 (m, 1H), 7.06 (d, J=8.09 Hz, 1H), 7.15-7.31 (m, 3H), 7.56 (d, J=2.15 Hz, 1H), 7.94-7.84 (m, 1H); $^{13}$C NMR (50 MHz, $CDCl_3$+$CCl_4$): δ 40.5, 48.7, 51.8, 73.6, 75.7, 119.4, 121.3, 125.8, 125.9, 126.8, 127.0, 127.5, 129.5 (2C), 133.5, 134.5, 139.0, 142.1, 154.7, 171.9; HRMS m/z: Calculated for $C_{20}H_{21}O_4$-325.1434. observed-325.1433.

Example 3

At first, 9-BBN (1.80 g, 14.81 mmol) was added to a well stirred solution of olefin 4 (4 g, 12.34 mmol) in anhydrous THF (40 mL) at room temperature (25° C.) and the reaction mixture was stirred for 24 h at 70° C. Then the reaction mixture was quenched with 3 M NaOH (0.54 g, 13.50 mmol) at 0° C., followed by the dropwise addition of 30% $H_2O_2$ (3.5 mL, 37.03 mmol) and the resulting solution was stirred for 6 h at room temperature (25° C.). The organic phase was separated and the aqueous layer extracted with ethyl acetate (3×20 mL). The combined organic phase was washed with brine (1×30 mL), dried over anhydrous $Na_2SO_4$, and the solvent was evaporated under reduced pressure. The crude product was subjected to flash column chromatography (pet ether-ethyl acetate, 7:3) to obtain diol 6 (3.54 g, 84%).

Colorless liquid; $^1$H NMR (200 MHz, $CDCl_3$+$CCl_4$): δ 1.20-1.56 (m, 2H), 2.08-2.28 (m, 1H), 2.64-2.89 (m, 1H), 3.36-3.64 (m, 4H), 3.67 (s, 3H), 4.84 (brs, 1H), 5.01 (d, J=15.4 Hz, 1H), 5.43 (d, J=15.4 Hz, 1H), 6.93 (d, J=7.2 Hz, 1H), 6.98-7.32 (m, 4H), 7.62 (d, J=2.15 Hz, 1H), 7.97 (d, J=7.5 Hz, 1H); $^{13}$C NMR (50 MHz, $CDCl_3$+$CCl_4$): δ 27.3, 40.4, 41.8, 52.0, 62.7, 73.6, 76.6, 121.2, 125.8, 126.2, 126.9 (2C), 128.2, 129.3 (2C), 134.4, 139.6, 143.3, 154.8, 172.6; HRMS m/z: Calculated for $C_{20}H_{22}O_5Na$-365.1359. observed-365.1360.

Example 4

The diol 6 (3 g, 2.5 mmol) was dissolved in dry DCM (30 mL) in an oven-dried flask under a nitrogen atmosphere and p-TSA (83 mg, 0.43 mmol) was added at room temperature (25° C.). The solution was stirred for additional 10 min. and then the reaction was quenched by the addition of water (20 mL). Resulting organic mass was extracted with DCM (3×20 mL), washed with brine, dried over anhydrous $Na_2SO_4$, filtered and column purified over silica gel (pet ether:ethyl acetate, 9:1) to furnish spiro ether 3 (2.81 g, 99%) as oil.

Colorless liquid; $^1$H NMR (400 MHz, $CDCl_3$+$CCl_4$): δ 1.87-1.99 (m, 2H), 2.56-2.72 (m, 2H), 3.59 (s, 2H), 3.69 (s, 3H), 4.20 (q, J=7.1 and 7.1 Hz, 1H), 4.31 (q, J=7.1 and 7.1 Hz, 1H), 5.02 (d, J=15.3 Hz, 1H), 5.56 (d, J=15.3 Hz, 1H), 6.97 (d, J=7.2 Hz, 1H), 7.03 (d, J=8.03 Hz, 1H), 7.10-7.26 (m, 3H), 7.51 (s, 1H), 7.74 (d, 0.5 Hz, 1H); $^{13}$C NMR (100 MHz, $CDCl_3$+$CCl_4$): δ 25.9, 40.7, 42.6, 51.9, 68.9, 72.9, 85.1, 121.4, 124.5, 126.2 (2C), 126.9, 127.0, 129.21, 129.27, 133.6, 140.2, 143.4, 153.9, 172.0; HRMS m/z: Calculated for $C_{20}H_{21}O_4$-325.1434. observed-325.1437.

Example 5

To a cold (0° C.), magnetically stirred solution of Spiro ether 3 (2 g, 6.12 mmol) in anhydrous DCM, was added anhydrous crystalline aluminium chloride (2.05 g, 15.43 mmol) in one portion under nitrogen. The resulting mixture was warmed to room temperature (25° C.) and the redorange reaction mixture was stirred at room temperature (25° C.) until the completion of reaction (7 h). The reaction mixture was then poured into an ice cooled 10% aqueous HCl and the aqueous layer was extracted with DCM. The combined organic extracts were dried over anhydrous $Na_2SO_4$, filtered and concentrated in vacuo. The crude reaction mixture was purified by flash silica gel column chromatography (pet ether:ethyl acetate, 7:3) resulted in allylic alcohol 2 (1.9 g, 95%).

White solid; $^1$H NMR (200 MHz, $CDCl_3+CCl_4$): δ 2.38-2.49 (m, 0.8H, E-Form), 2.63-2.73 (m, 1.2H, Z-Form), 3.53 (s, 2H), 3.68 (s, 3H), 3.75 (m, 0.8H, E-Form), 3.81 (t, J=6.3 Hz, 1.2H), 5.19 (brs, 2H), 5.73 (t, J=7.8 Hz, 0.6H, Z-Form), 6.06 (t, J=7.8 Hz, 0.4H, E-Form), 6.70 (d, J=8.2 Hz, 0.4H, E-Form), 6.79 (d, J=8.2 Hz, 0.6H, Z-Form), 7.00-7.34 (m, 6H), HRMS m/z: Calculated for $C_{20}H_{21}O_4$-325.1434. observed-325.1437.

Example 6

To allyl alcohol 2 (1 g, 3.08 mmol) in pyridine (16 mL) was added methanesulfonyl chloride (0.95 mL, 11.72 mmol) gradually at 0° C. The reaction mixture was heated to room temperature (25° C.) and stirred for 2 h. The mixture was quenched with water (5 mL) and then extracted with ethyl acetate (20×2). The organic layer was washed with saturated aqueous NaCl (10 mL) and concentrated. To a solution of obtained oil in MeOH (20 mL) was add 50% aqueous dimethylamine (5.2 mL, 18.0 equiv) and the mixture was stirred under reflux for 3 h. The solvent was evaporated and extracted with ethyl acetate (20×2). The organic layer was washed with saturated aqueous NaCl (10 mL) and dried over anhydrous $Na_2SO_4$, filtered and concentrated under reduced pressure. The crude reaction mixture was purified by flash silica gel column chromatography (MeOH) resulted in 7 (0.91 g, 84%). Overall yield: 59% pale yellow liquid; $^1$H NMR (200 MHz, $CDCl_3+CCl_4$): 2.15 (s, 2H), 2.24 (s, 4H), 2.31-2.62 (m, 4H), 3.51 (s, 2H), 3.67 (s, 3H), 4.73 (brs, 1H), 5.45 (brs, 1H), 5.69 (t, J=7.1 Hz, 0.6H, Z-Form), 6.02 (t, J=6.9 Hz, 0.4H, E-Form), 6.69 (d, J=8.3 Hz, 0.4H, E-Form), 6.78 (d, J=8.3 Hz, 0.6H, Z-Form), 6.98-7.37 (m, 6H).

Example 7

A mixture of 7 (2.87 g, 8.2 mmol, E/Z=1/1.5), MeOH (100 mL), 10 N NaOH (3.0 mL, 30 mmol), and water (20 mL) was refluxed for 1 h and then concentrated under reduced pressure. The residue (E/Z=1/1.5) was diluted with $H_2O$ and the solution was neutralized with 4 N HCl. The crude mixture (2.6 g, 7.7 mmol, E/Z 1/1.5) on subsequent desalination with HP-10 ($H_2O$ and then MeOH as eluent) was dissolved in 2-propanol (40 mL) containing p-TsOH.$H_2O$ (1.47 g, 7.7 mmol). The solution was stirred at room temperature (27° C.) and the resultant precipitate was collected by filtration. The crude product was recrystallized from 2-propanol to give 2.16 g (55%) of (Z)-2-(11-(3-(dimethylamino)propylidene)-6,11-dihydrodibenzo[b,e]oxepin-2-yl)acetic acid p-toluenesulfonate mp 185-187° C. The salt was added portionwise to aqueous $NaHCO_3$, with ice cooling and the resultant solution was neutralized with 4 N HCl. The crude product was desalinated with HP-10 and recrystallized successively from 2-propanol and water to give 1.14 g (66%) of the free base 8 mp 188-189.5"C; $^1$H NMR (DMSO-$d_6$): 2.15 (s, 6H), 2.40-2.60 (m, 4H), 3.45 (8, 2H), 5.00-5.55 (br, 2H), 5.66 (t, J=6.7 Hz, 1H), 6.75 (d, J=8.1 Hz, 1H), 7.0-7.1 (m, 2H), 7.2-7.4 (m, 4H); MS m/z 337 (M+). The free base 8 (1.14 g, 35 mmol) was added to a 8 N solution of HCl in 2-propanol (0.8 mL, 64 mmol) and the mixture was stirred at room temperature (27° C.). After being concentrated, the residue was recrystallized from acetone-water (2/1) to give 0.93 g (80%) of 8 as hydrochloride salt: mp 248° C. dec. (Compound 1). The E/Z ratio was determined by analyzing the $^1$H NMR spectrum of compound 7, by integration of characteristic protons at δ 5.69 (Z) and δ 6.02 (E) which appear as triplets.

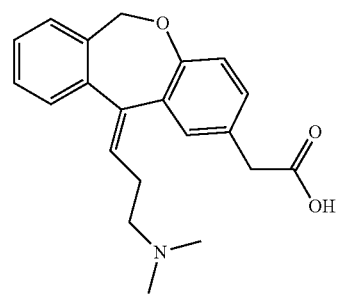

8

ADVANTAGES OF THE INVENTION

1. Avoids expensive metal catalysts.
2. Avoids hazardous reagents and reaction conditions.
3. Improved yield of preferred diastereomer.

We claim:
1. An improved process for synthesis of olopatadine comprising the steps of:
   a. treating Isoxepac (5), 2-(11-oxo-6,11-dihydrodibenzo[b,e]oxepin-2-yl)acetic acid with thionyl chloride in the ratio ranging between 2 to 4 in the presence of an alcohol at room temperature in the range of 15 to 30° C. for period in the range of 12 to 24 hours to yield the corresponding ester;

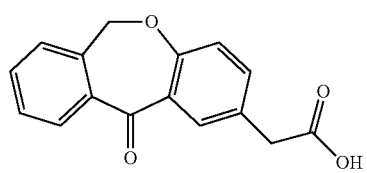

5 b. treating the ester of step (a) with allyl bromide using Zn in a solvent conducting Barbier reaction to obtain the allylic alcohol 4;

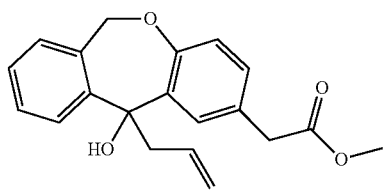

4 c. Hydroborating the allyl alcohol (4) as obtained in step (b) using 9-BBN (9-Borabicyclo(3.3.1)nonane)/diborane quenched by sodium hydroxide and hydrogen peroxide to obtain diol 6;

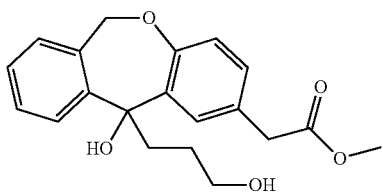

6 d. treating diol 6 as obtained in step (c) with catalytic p-toluenesulfonic acid to form a spiro tetrahydrofuran ring 3 in almost quantitative yield;

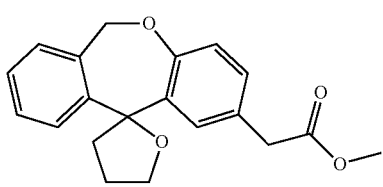

3 e. treating compound 3 as obtained in step (d) with AlCl₃ as Lewis acid in dichloromethane to yield olefin 2 and satisfactory E/Z ratio of 1 to 1.5;

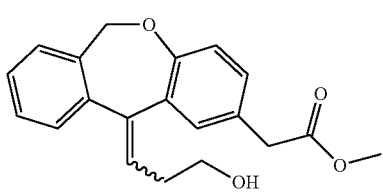

2 f. subjecting compound 2 of step (e) to mesylation and dimethyl amination to result in compound 7

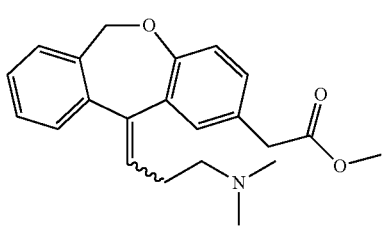

7 in the range of 55 to 60%;

g. treating compound 7 as obtained in step (f) with aqueous NaOH to yield the corresponding carboxylic acid, treating the acid with p-toluenesulfonic acid to yield the corresponding p-toluenesulfonate, crystallizing the p-toluenesulfonate to isolate the Z-isomer of the p-toluenesulfonate, treating the Z-isomer of the p-toluenesulfonate with NaHCO₃ to yield the free base 8

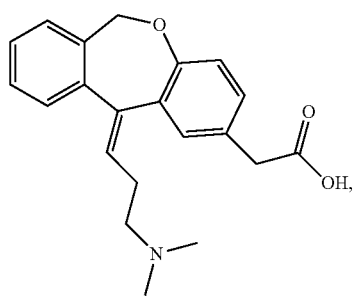

8 and treating free base 8 with aqueous HCl to give 1 with E:Z ratio of 1:1.5

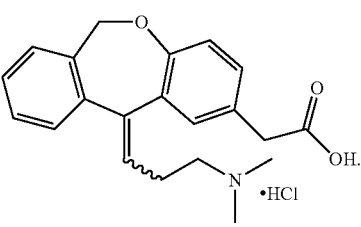

1

2. The process according to claim 1, wherein the alcohol used in step (a) is methanol.

3. The process according to claim 1, wherein the solvent used in step (b) is dimethyl formamide (DMF).

* * * * *